US00PP26001P2

(12) United States Plant Patent
Fisher

(10) Patent No.: US PP26,001 P2
(45) Date of Patent: Oct. 20, 2015

(54) ***MANDEVILLA* PLANT NAMED 'FGVP1'**

(50) Latin Name: *Mandevilla splenders*
Varietal Denomination: FGVP1

(75) Inventor: Wes Fisher, Sebring, FL (US)

(73) Assignee: Fury Genetics LLC, Hawthorne, FL (US)

( * ) Notice: Subject to any disclaimer, the term of this patent is extended or adjusted under 35 U.S.C. 154(b) by 161 days.

(21) Appl. No.: 13/573,172

(22) Filed: Aug. 27, 2012

(51) Int. Cl.
*A01H 5/00* (2006.01)

(52) U.S. Cl.
USPC ..... Plt./232

(58) Field of Classification Search
USPC ..... Plt./232
CPC ..... A01H 5/02
See application file for complete search history.

(56) References Cited

U.S. PATENT DOCUMENTS

PP19,698 P2 * 2/2009 Fisher et al. ..... Plt./232
PP20,776 P2 * 2/2010 Brown ..... Plt./232

* cited by examiner

*Primary Examiner* — Keith O. Robinson
(74) *Attorney, Agent, or Firm* — C. A. Whealy

(57) ABSTRACT

A new and distinct cultivar of *Mandevilla* plant named 'FGVP1', characterized by its initially upright to outwardly spreading and strongly vining plant habit; medium green-colored leaves; pink-colored flowers; and good garden performance.

2 Drawing Sheets

Botanical designation: *Mandevilla splendens.*
Cultivar denomination: 'FGVP1'.

BACKGROUND OF THE INVENTION

The present invention relates to a new and distinct cultivar of *Mandevilla* plant, botanically known as *Mandevilla splendens* and hereinafter referred to by the name 'FGVP1'.

The new *Mandevilla* plant is a naturally-occurring branch mutation of *Mandevilla splendens* 'DIP 79', disclosed in U.S. Plant Pat. No. 19,698. The new *Mandevilla* plant was discovered and selected by the Inventor on a single plant within a population of plants of 'DIP 79' grown in a controlled greenhouse environment in Sebring, Fla. on Jul. 9, 2008. The new *Mandevilla* plant was selected on the basis of its vining plant habit and flower color.

Asexual reproduction of the new *Mandevilla* plant by tip cuttings in a controlled greenhouse in Sebring, Fla. since Jul. 10, 2008 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'FGVP1'. These characteristics in combination distinguish 'FGVP1' as a new and distinct *Mandevilla* plant:

1. Initially upright to somewhat outwardly spreading and strongly vining plant habit.
2. Medium green-colored leaves.
3. Pink-colored flowers.
4. Good garden performance.

Plants of the new *Mandevilla* differ primarily from plants of the parent, 'DIP 79', in the following characteristics:

1. Plants of the new *Mandevilla* are more strongly vining than plants of 'DIP 79'.
2. Plants of the new *Mandevilla* and 'DIP 79' differ in flower color as plants of 'DIP 79' have red-colored flowers.

Plants of the new *Mandevilla* can be compared to plants of the *Mandevilla hybrida* 'Ginger', disclosed in U.S. Plant Pat. No. 20,776. In side-by-side comparisons conducted in Sebring, Fla., plants of the new *Mandevilla* differed from plants of 'Ginger' in the following characteristics:

1. Plants of the new *Mandevilla* were more strongly vining than plants of 'Ginger'.
2. Plants of the new *Mandevilla* had shorter internodes than plants of 'Ginger'.
3. Plants of the new *Mandevilla* had smaller and lighter green-colored leaves than plants of 'Ginger'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'FGVP1' grown in a container.

The photograph on the second sheet is a close-up view of a typical flowering plant of 'FGVP1'.

DETAILED BOTANICAL DESCRIPTION

Plants used for the aforementioned photograph and following description were grown during the spring and summer in 1.5-gallon containers in an outdoor nursery in Fort Worth, Tex. and under cultural practices which closely approximate commercial production conditions. During the production of the plants, day temperatures ranged from 24° C. to 38° C. and night temperatures ranged from 21° C. to 24° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla splendens* 'FGVP1'.

Parentage: Naturally-occurring branch mutation of *Mandevilla splendens* 'DIP 79', disclosed in U.S. Plant Pat. No. 19,698.

Propagation:

*Type*.—By tip cuttings.

*Time to initiate roots, summer*.—About 14 to 16 days at 29° C. to 32° C.

*Time to initiate roots, winter*.—About 17 to 18 days at 24° C.

*Time to produce a rooted young plant, summer*.—About 35 days at 29° C. to 32° C.

*Time to produce a rooted young plant, winter*.—About 45 days at 24° C.

*Root description*.—Fibrous to fleshy, medium in thickness; white in color.

*Rooting habit*.—Moderately freely branching; medium density.

Plant description:

*Plant and growth habit*.—Initially upright to somewhat outwardly spreading and strongly vining plant habit that requires support; relatively compact; moderately vigorous growth habit.

*Vine length*.—About 97 cm to 142 cm.

*Plant diameter (spread)*.—About 39 cm to 52 cm.

*Lateral branch description*.—Length: About 69 cm to 88 cm. Diameter: About 3 mm. Internode length: About 3.5 cm to 12 cm. Strength: Flexible, strong. Texture, young stems: Smooth. Texture, developed stems: Woody. Color, young stems: Close to 153A to 153B becoming closer to 175A with development. Color, woody stems: Close to 183A.

Leaf description:

*Arrangement*.—Opposite, simple.

*Length*.—About 5.5 cm to 6 cm.

*Width*.—About 2.8 cm to 3.6 cm.

*Shape*.—Elliptic to ovate.

*Apex*.—Cuspidate.

*Base*.—Obtuse.

*Margin*.—Entire.

*Texture, upper and lower surfaces*.—Smooth, glabrous.

*Venation pattern*.—Pinnate.

*Color*.—Developing leaves, upper surface: Close to more green than 146A. Developing leaves, lower surface: Close to 146B. Fully expanded leaves, upper surface: Close to N137A; venation, close to 146A. Fully expanded leaves, lower surface: Close to 146A to 146B; venation, close to 146B to 146C.

*Petioles*.—Length: About 1.2 cm to 1.5 cm. Diameter: About 2 mm. Texture, upper and lower surfaces: Smooth, glabrous. Color, upper and lower surfaces: Close to 144A.

Flower description:

*Flower type and habit*.—Single salverform flowers; flowers arranged in terminal and axillary clusters; flowers face mostly outwardly; freely flowering habit.

*Natural flowering season*.—Plants of the new *Mandevilla* flower continuously year-round in Florida.

*Flower longevity on the plant*.—Flowers last about seven to nine five days; flowers not persistent.

*Fragrance*.—Faint, mint-like.

*Flowers*.—Appearance: Flared trumpet, corolla fused, five-parted; flowers salverform and roughly star-shaped. Diameter: About 6 cm to 8 cm. Depth (length): About 4.5 cm to 5.5 cm. Throat diameter: About 1.6 cm. Tube length: About 3.6 cm. Tube diameter, base: About 4 mm.

*Flower buds*.—Length: About 3.3 cm. Diameter: About 4 mm. Shape: Cylindrical, pointed. Color: Towards the base, close to 144A; towards the apex, close to 60A.

*Corolla*.—Arrangement: Single whorl of five petals, fused into flared trumpet; petals reflexing. Petal lobe length: About 2.4 cm to 3 cm. Petal lobe width: About 1.9 cm to 2.4 cm. Petal lobe shape: Roughly spatulate. Petal apex: Obtuse with truncate tendencies. Petal margin: Entire. Petal texture, upper and lower surfaces: Smooth, glabrous; velvety. Throat and tube texture: Smooth, glabrous. Color: Petal, when opening, upper surface: Close to 60A. Petal, when opening, lower surface: Close to 63A. Petal, fully opened, upper surface: Close to 62A to 62B; towards the apex, close to 60A to 60B. Petal, fully opened, lower surface: Close to 63B. Throat: Close to 17A and 17B; towards the petal lobes, close to 62A. Tube: Close to 63D; towards the base, close to 45A.

*Sepals*.—Arrangement and appearance: Five per flower in a single whorl; fused towards the base. Length: About 7.5 mm to 10 mm. Width: About 2.5 mm to 3 mm. Shape: Lanceolate. Apex: Acute; reflexed. Margin: Entire. Texture, inner and outer surfaces: Smooth, glabrous. Color, inner surface: Close to 145B; towards the apex, close to 45A. Color, outer surface: Close to 144A; towards the apex, close to 45A.

*Peduncles*.—Length: About 1.1 cm. Diameter: About 2 mm. Texture: Smooth, glabrous. Strength: Flexible, but strong. Aspect: Initially upright, becoming more outwardly arching with the weight of the developing flower. Color: Close to 146A tinged with close to 175A to 175B.

*Reproductive organs*.—Stamens: Quantity and arrangement: Typically five; filaments fused to corolla; anthers, connivent. Filament length: About 1 cm to 2 cm. Filament color: Close to 155D. Anther shape: Elongated oblong. Anther length: About 4 mm to 7.5 mm. Anther color: Close to 12A. Pollen amount: None observed. Pistils: Quantity: Typically one. Pistil length: About 2.5 cm. Stigma shape: Oblong to rounded. Stigma color: Close to 11D. Style length: About 2 cm. Style color: Close to 155D. Ovary color: Close to 145A to 145B.

*Seeds and fruits*.—Seed and fruit production have not been observed on plants of the new *Mandevilla*.

Disease & pest resistance: Plants of the new *Mandevilla* have not been observed to resistant to pathogens and pests common to *Mandevilla* plants.

Temperature tolerance: Plants of the new *Mandevilla* have been observed to tolerate temperatures from about 1° C. to about 40° C.

It is claimed:

1. A new and distinct *Mandevilla* plant named 'FGVP1' as illustrated and described.

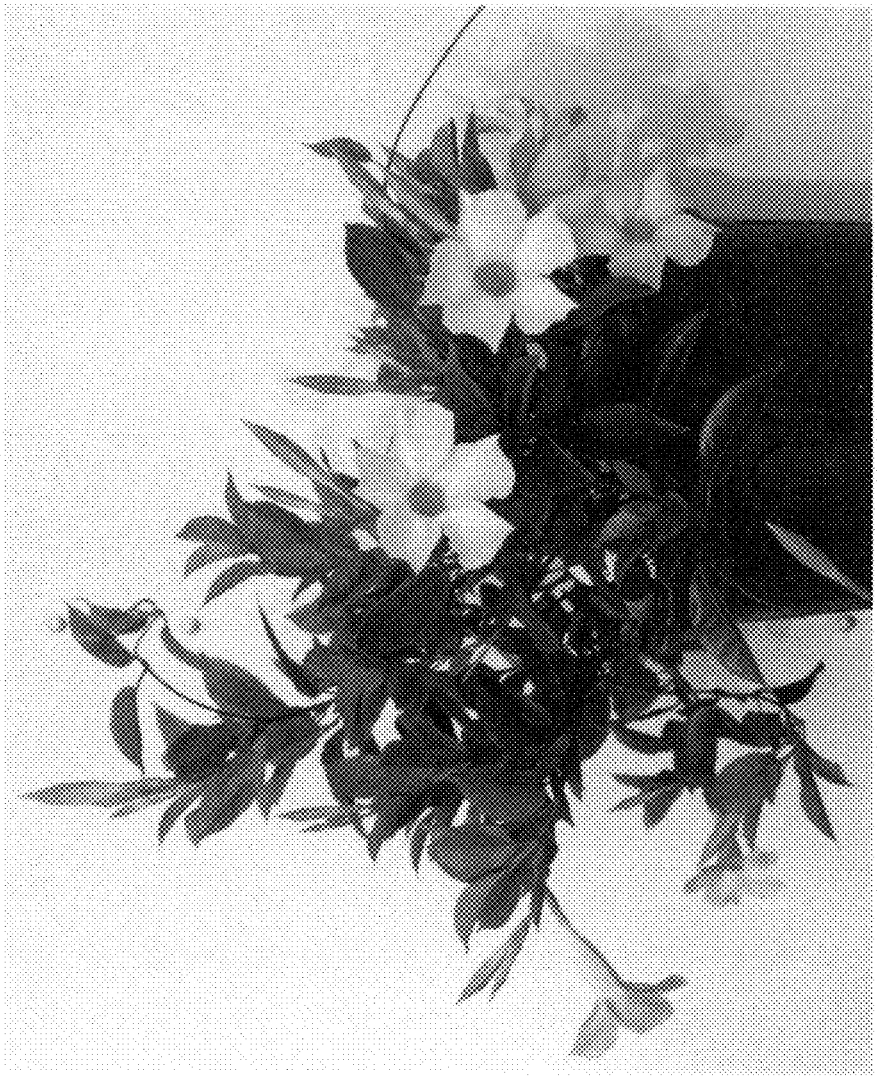

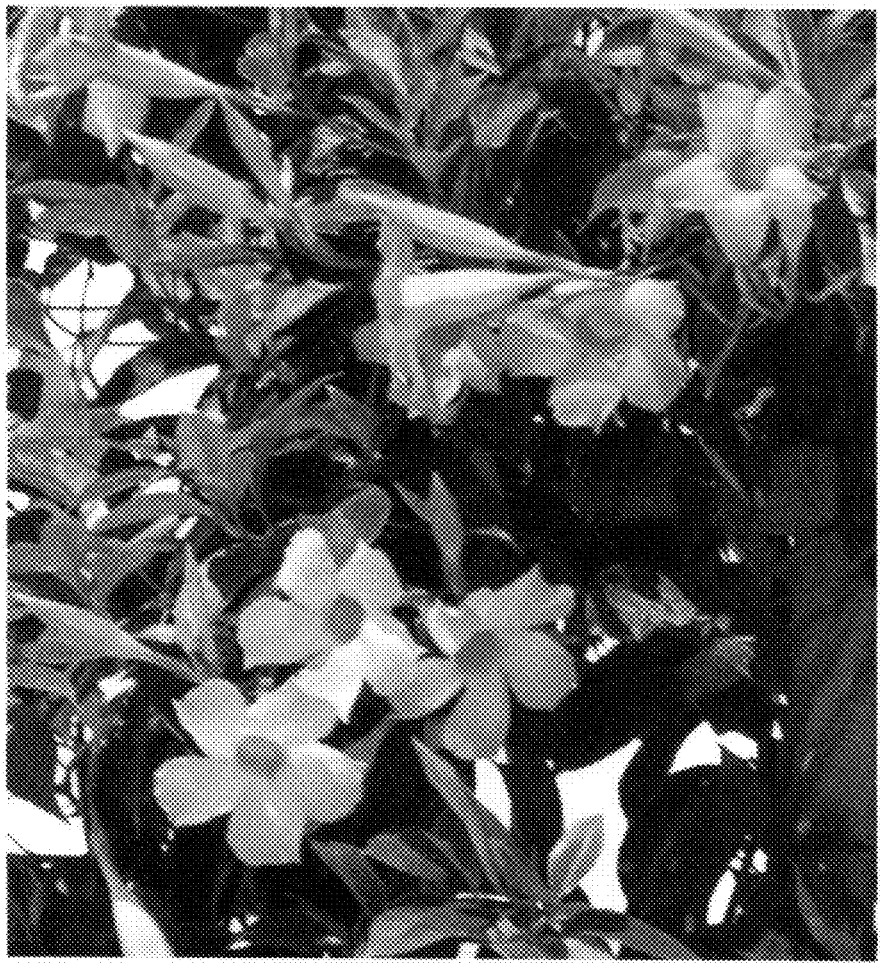

* * * * *